United States Patent
Arnin et al.

(10) Patent No.: US 7,491,238 B2
(45) Date of Patent: Feb. 17, 2009

(54) ADJUSTABLE SPINAL PROSTHESIS

(75) Inventors: Uri Arnin, Kiryat Tivon (IL); Yuri Sudin, Modiin (IL); Shai Fleischer, Haifa (IL)

(73) Assignee: Impliant Ltd., Ramat Poleg, Netanya (IL)

( * ) Notice: Subject to any disclaimer, the term of this patent is extended or adjusted under 35 U.S.C. 154(b) by 529 days.

(21) Appl. No.: 11/019,276

(22) Filed: Dec. 23, 2004

(65) Prior Publication Data

US 2006/0142759 A1 Jun. 29, 2006

(51) Int. Cl.
*A61F 2/44* (2006.01)
(52) U.S. Cl. .................................................. 623/17.14
(58) Field of Classification Search ..... 62/17.11–17.16; 606/61
See application file for complete search history.

(56) References Cited

U.S. PATENT DOCUMENTS

| | | | | |
|---|---|---|---|---|
| 4,759,769 A | * | 7/1988 | Hedman et al. | 623/17.13 |
| 4,932,975 A | * | 6/1990 | Main et al. | 623/17.12 |
| 5,057,109 A | | 10/1991 | Olerud et al. | |
| 5,683,465 A | * | 11/1997 | Shinn et al. | 623/17.14 |
| 6,296,644 B1 | | 10/2001 | Saurat et al. | |
| 6,454,807 B1 | * | 9/2002 | Jackson | 623/17.15 |
| 2002/0143330 A1 | * | 10/2002 | Shluzas | 606/61 |
| 2004/0002708 A1 | * | 1/2004 | Ritland | 606/61 |
| 2004/0116928 A1 | * | 6/2004 | Young et al. | 606/61 |
| 2004/0153160 A1 | * | 8/2004 | Carrasco | 623/17.15 |
| 2005/0102028 A1 | * | 5/2005 | Arnin et al. | 623/17.13 |
| 2005/0119748 A1 | * | 6/2005 | Reiley et al. | 623/17.11 |
| 2005/0228381 A1 | * | 10/2005 | Kirschman | 606/61 |
| 2005/0267579 A1 | * | 12/2005 | Reiley et al. | 623/17.11 |
| 2005/0277930 A1 | * | 12/2005 | Parsons | 606/61 |
| 2006/0052785 A1 | * | 3/2006 | Augostino et al. | 606/61 |
| 2006/0100707 A1 | * | 5/2006 | Stinson et al. | 623/17.11 |
| 2006/0129239 A1 | * | 6/2006 | Kwak | 623/17.13 |

* cited by examiner

*Primary Examiner*—Eduardo C Robert
*Assistant Examiner*—Nicholas Woodall
(74) *Attorney, Agent, or Firm*—Dekel Patent Ltd.; David Klein

(57) ABSTRACT

Apparatus including a first spinal prosthetic member attachable to a first spinal structure, and a second spinal prosthetic member attachable to a second spinal structure, the first and second spinal prosthetic members being movably attached to one another with a fastening device, the fastening device having a non-tightened position which permits spatial movement of the first and second spinal prosthetic members with respect to one another at a desired orientation, and a tightened position which fixes the first and second spinal prosthetic members at the desired orientation.

3 Claims, 4 Drawing Sheets

ADJUSTABLE SPINAL PROSTHESIS

FIELD OF THE INVENTION

The present invention is generally related to apparatus and methods for spinal prostheses.

BACKGROUND OF THE INVENTION

Through disease or injury, the laminae, spinous process, articular processes, or facets of one or more vertebral bodies can become damaged, such that the vertebrae no longer articulate or properly align with each other. This can result in an undesired anatomy, loss of mobility, and pain or discomfort. For example, spinal stenosis, as well as spondylosis, spondylolisthesis, osteoarthritis and other degenerative phenomena may cause back pain, especially lower back pain, such as in the lumbosacral (L4-S1) region. Such phenomena may be caused by a narrowing of the spinal canal by a variety of causes that result in the pinching of the spinal cord and/or nerves in the spine.

The prior art has many spinal prostheses designed to help the patient with various back problems. One problem addressed by the prior art is that of the spinal lordosis.

A normal and healthy spine has a natural curvature referred to as lordosis. As a result of the curvature, opposing vertebrae are positioned with their end plates in nonparallel alignment depending upon the position in the spine. For example, in the lumbar region of the spine, the end plates of the L-4 and L-5 vertebrae may be at an angle of about 3-15°. Similarly, the opposing end plates of the L-5 and S-1 vertebrae may have a lordotic angle of about 8-16°. The actual amount of lordosis varies with the location of the spine and varies from patient to patient.

A problem that needs to be addressed in spinal prosthetic devices is that of matching or correcting the lordotic angle. The prior art accomplishes this with custom-built prostheses with a predetermined lordotic angle.

For example, U.S. Pat. Nos. 6,740,091 and 6,165,219 to Kohrs, et al., assigned to Sulzer Spine-Tech Inc. (Minneapolis, Minn.) describe a lordotic implant that has a frustoconical shape with external threads. Prior to placement of the implant, vertebrae are distracted in a manner to provide a desired lordosis between the vertebrae. The pre-distracted vertebrae are then tapped to provide a tapped bore having a geometry matching the conical geometry of the implant. The threaded implant is then placed within the pre-tapped conical bore.

US Patent Application 20030028250 to Reilley et al., describes cephalad and caudal vertebral facet joint prostheses. The prostheses are customized to provide a pre-defined lordotic angle and a pre-defined pedicle entry angle.

Reilley et al. states that the prostheses can be "adjusted" to create a desired lordotic angle. Quoting from paragraph 27 of Reilley et al., "Various other aspects of the invention provide cephalad and/or caudal prostheses that readily adapt to or physically change the specific anatomy of an individual. For example, a cephalad prosthesis can be capable of being adjusted in either an anterior or posterior direction relative to a vertebra. As another example, a cephalad prosthesis and/or a caudal prosthesis can provide for lateral (left and right) adjustment, to accommodate or create variances in the distance between the right and left pedicles of a single vertebra. Furthermore, a cephalad prosthesis and/or a caudal prosthesis can provide vertical (up and down) adjustment, to accommodate or create variations in interpedicle distance between adjacent vertebra. Or, as another example, a cephalad prosthesis and a caudal prosthesis can together create a desired lordotic angle between adjacent vertebral bodies, or create a pre-defined pedicle entry angle for mounting each prosthesis on a given vertebral body."

However, the "adjustment" that Reilley et al. provides is nothing more than a prosthesis pre-manufactured and customized to a particular lordotic angle. The "adjustment" means selecting the desired angle and making a fixed, non-adjustable prosthesis according to the selected angle. This is evident, for example, from FIG. 16 of Reilley et al. and the accompanying text in paragraphs 110 and 112-113, which describe "Lordotic Angle Adjustment": "In the illustrated embodiment (see FIG. 16), the openings 50 and 56 of adjacent cephalad and caudal prostheses 36 and 38 are mutually oriented in nonparallel planes along the inferior-superior axis. The non-parallel orientation of the planes defines between the fixation elements 52 and 58, when supported by the openings 50 and 56, an angle that results a desired lordotic angle. The mutual orientation and the resulting angle defined depends upon the intended location of the prostheses 36 and 38 along the spinal column 10. The defined angle is designated angle "L" in FIG. 16. In FIG. 16, the angle L is defined by orienting the plane of the opening 50 of the cephalad prosthesis 36 generally parallel to the inferior-superior axis, while tilting the plane of the opening 56 of the caudal prosthesis 38 generally downward at an acute inferior angle relative to the inferior-superior axis." It is noted that "tilting the plane of the opening 56 of the caudal prosthesis 38" does not refer to any in-situ tilting, rather machining the prosthesis to the desired angle.

SUMMARY OF THE INVENTION

The present invention seeks to provide a novel spinal prosthesis that may be adjusted in-situ, such as but not limited to, adjustment to a desired lordotic angle, as is described more in detail hereinbelow.

There is thus provided in accordance with an embodiment of the invention apparatus including a first spinal prosthetic member attachable to a first spinal structure, and a second spinal prosthetic member attachable to a second spinal structure, the first and second spinal prosthetic members being movably attached to one another with a fastening device, the fastening device having a non-tightened position which permits spatial movement of the first and second spinal prosthetic members with respect to one another at a desired orientation, and a tightened position which fixes the first and second spinal prosthetic members at the desired orientation.

The apparatus may include other features. For example, the first and second spinal prosthetic members may be pivotable with respect to one another about a first pivot axis to define an angle between the first and second spinal prosthetic members that corresponds to a lordotic angle between the first and second spinal structures. The first and second spinal prosthetic members may articulate with respect to one another along non-straight surfaces thereof and the fastening device, in its tightened position, may fix the first and second spinal prosthetic members at a desired orientation along the non-straight surfaces. The non-straight surfaces may include a convex surface formed on the first spinal prosthetic member and a concave surface formed on the second spinal prosthetic member. The first and second spinal prosthetic members may also be pivotable with respect to one another about a second pivot axis angled at a non-zero angle with respect to the first pivot axis. The fastening device may include a threaded fastener and a spacer member, the spacer member having a non-straight surface that interfaces with and is tightened by the threaded fastener against the non-straight surfaces of the first and second spinal prosthetic members.

In accordance with an embodiment of the invention the first spinal prosthetic member may include a unitary body that includes a flexure assembly positioned between first and second attachment members, wherein flexure of the flexure assembly permits movement of the first attachment member relative to the second attachment member, the first attachment member including at least one attachment point attachable to the first spinal structure, and the second attachment member being movably attached to the second spinal prosthetic member with the fastening device. The flexure assembly may include an elastomeric boot placed at least partially around the first and second attachment members, the boot being connected to the first and second attachment members. The flexure assembly may flex omnidirectionally. The second spinal prosthetic member may include a unitary body that includes laterally extending arms including mounting hardware positioned along the arms.

BRIEF DESCRIPTION OF THE DRAWINGS

The present invention will be understood and appreciated more fully from the following detailed description, taken in conjunction with the drawings in which.

DETAILED DESCRIPTION OF EMBODIMENTS

Reference is now made to FIGS. 1-4, which illustrate a spinal prosthesis 10, constructed and operative in accordance with an embodiment of the present invention.

Figure 1:
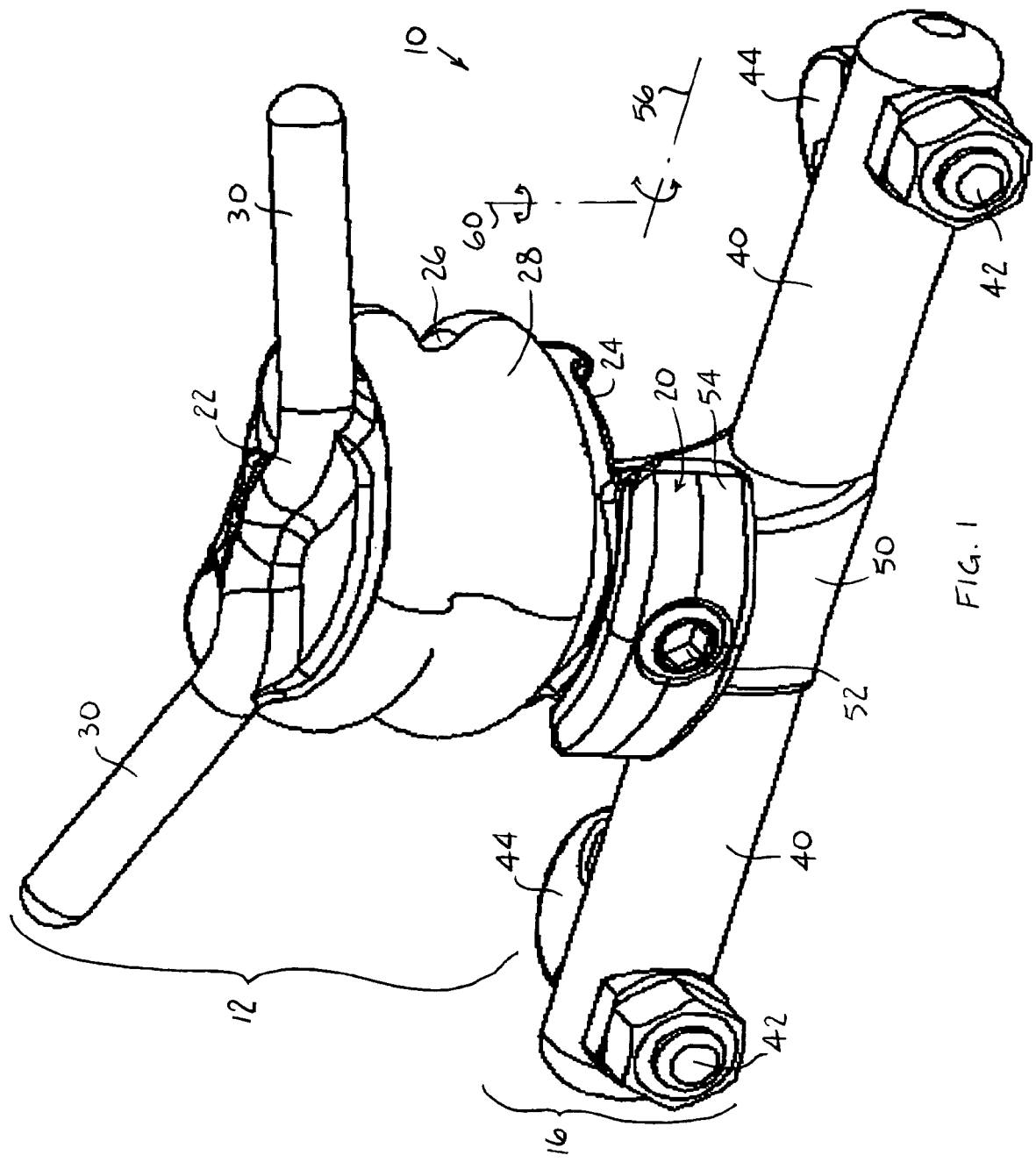
FIGS. 1 and 2 are simplified pictorial illustrations of a spinal prosthesis, seen at front and rear perspective views, constructed and operative in accordance with an embodiment of the present invention.
Figure 2:
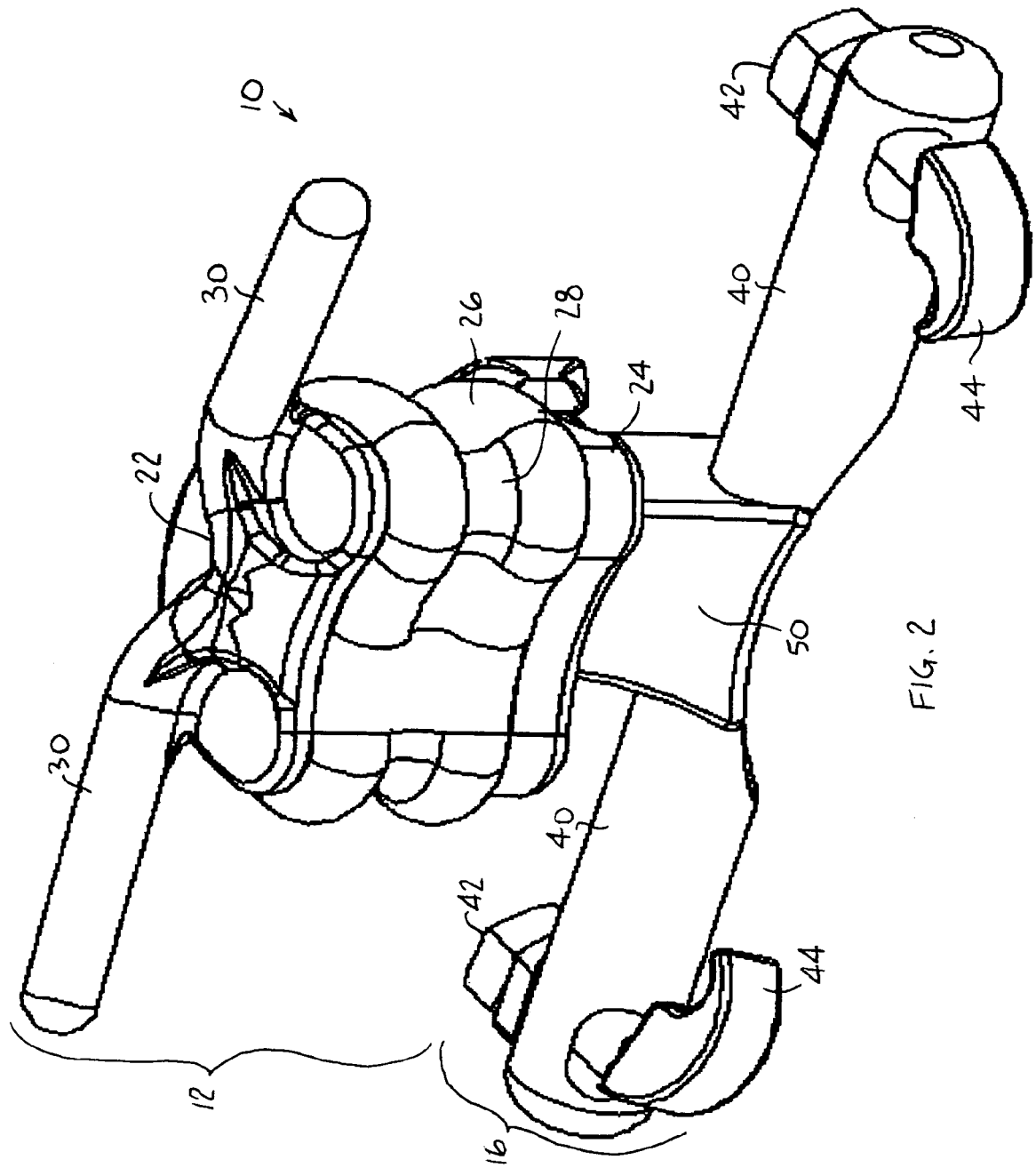
Figure 3:
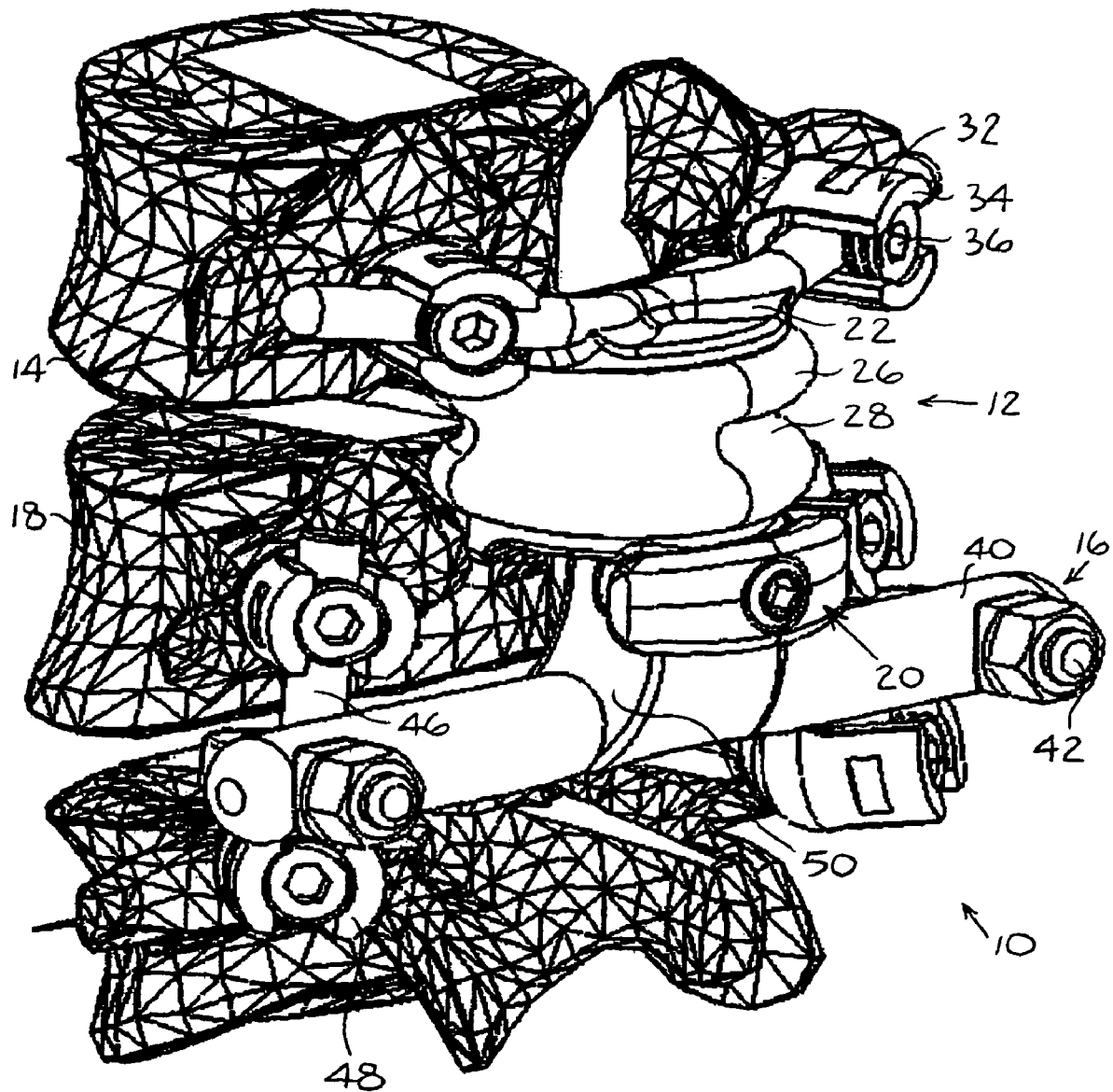
FIGS. 3 and 4 are simplified pictorial illustrations of the spinal prosthesis of FIGS. 1 and 2, attached to spinal structure with pedicle screws, respectively in exploded perspective and side views.
Figure 4:
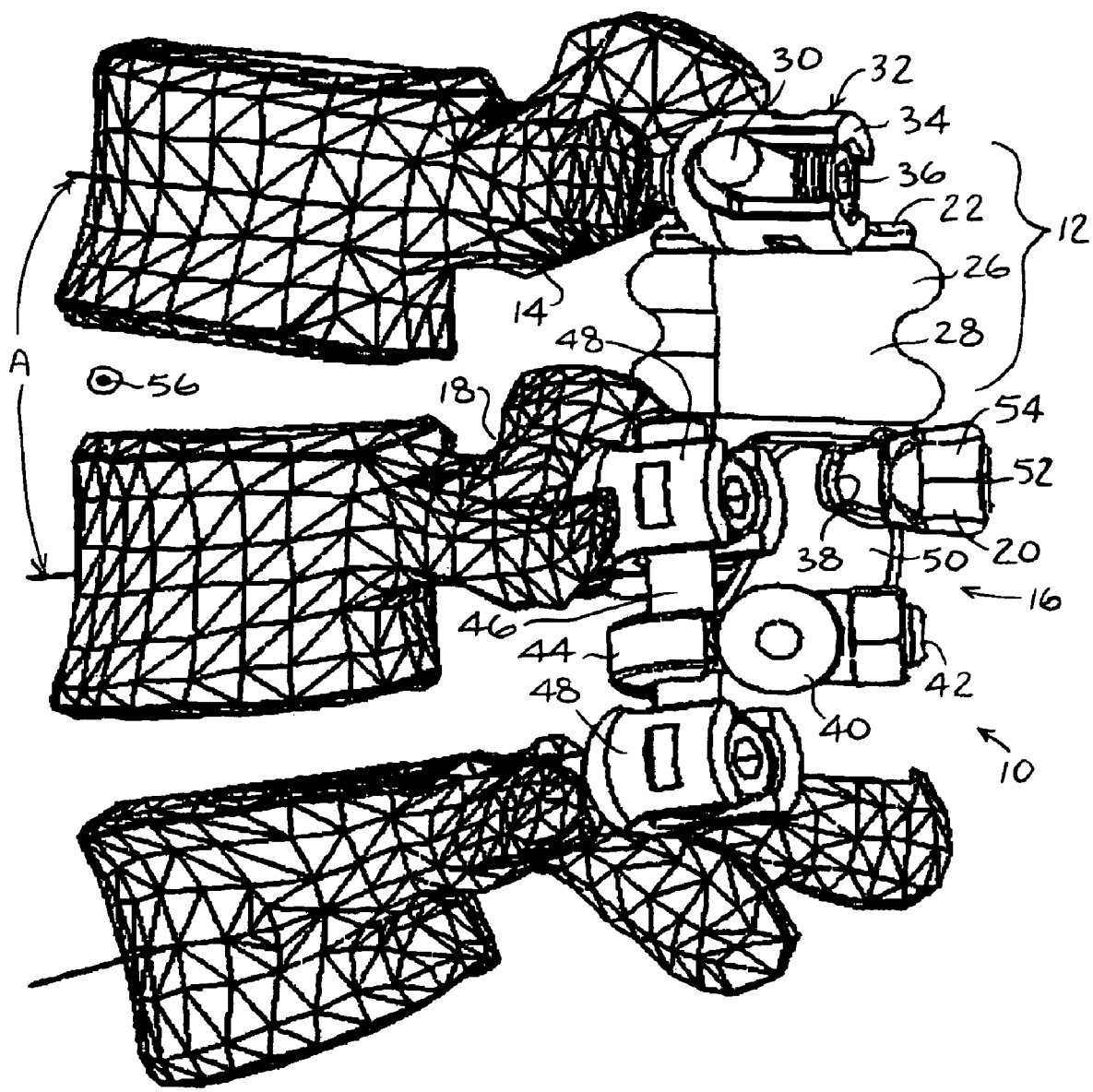

The spinal prosthesis 10 may include a first spinal prosthetic member 12, which may be attached to a first spinal structure 14, such as but not limited to, a vertebra (e.g., L3, as seen in FIG. 4). The spinal prosthesis 10 may also include a second spinal prosthetic member 16, which may be attached to a second spinal structure 18, such as but not limited to, a vertebra (e.g., L4, as seen in FIG. 4). One non-limiting way of attaching the first and second spinal prosthetic member 12 and 16 to the first and second spinal structures 14 and 18 is described more in detail hereinbelow.

The first and second spinal prosthetic members 12 and 16 may be movably attached to one another with a fastening device 20. As will be described more in detail hereinbelow, the fastening device 20 has a non-tightened position which permits spatial movement of the first and second spinal prosthetic members 12 and 16 with respect to one another at a desired orientation, and a tightened position which fixes the first and second spinal prosthetic members 12 and 16 at the desired orientation.

In the non-limiting illustrated embodiment, the first spinal prosthetic member 12 may include a first (e.g., upper or superior) attachment member 22 and a second (e.g., lower or inferior) attachment member 24. The attachment members 22 and 24 may be rigid or non-rigid, formed of materials including, but not limited to, a biocompatible material such as a metal, e.g., stainless steel, titanium or titanium alloy, cobalt chromium alloys, plastics or other hard, rigid materials or any combination of the above.

A flexure assembly 26 may be placed between and may be integrally formed with or attached to the first and second attachment members 22 and 24. A boot 28 may be placed at least partially or fully around the first and second attachment members 22 and 24. The boot 28 may have any suitable shape or size, such as but not limited to, a ring, a stocking, an ellipsoid and other shapes. The flexure assembly 26 may be constructed of a compliant, elastomeric material including, but not limited to, polyurethane containing materials, silicone containing materials, polyethylene based elastomers, hydrogels, and polypropylene containing materials. Boot 28 may also be made of a compliant material, such as but not limited to, an elastomer (e.g., polyurethane) or cloth (woven or nonwoven synthetic or natural fibers). The flexure assembly 26 may permit omnidirectional flexure of the first spinal prosthetic member 12.

The first attachment member 22 may include at least one attachment point attachable to the first spinal structure 14, such as but not limited to, a pair of rounded prongs 30 from which depending pedicle screws 32 (FIGS. 3 and 4) that screw into the first spinal structure 14 (e.g., pedicles). The pedicle screws 32 may comprise, without limitation, polyaxial pedicle screws, e.g., made of titanium or titanium alloy, commercially available in many sizes and shapes from many manufacturers. It is noted that titanium is highly resistant to corrosion and fatigue, and is MRI compatible. The pedicle screw 32 may have a mobile, swivel head 34, whose ability to swivel may help avoid vertebral stress. The swivel heads 34 may be rotatably attached to the rounded prongs 30 by means of lock nuts 36 that mate with heads 34.

In the non-limiting illustrated embodiment, the second attachment member 24 may include a base with an extension 38 that is formed with a non-straight (e.g., convexly curved) interface surface for interfacing and articulating with the second spinal prosthetic member 16. The second attachment member 24 may be rigid or non-rigid, formed of materials including, but not limited to, a biocompatible material such as a metal, e.g., stainless steel, titanium or titanium alloy, cobalt chromium alloys, plastics or other hard, rigid materials or any combination of the above. The second attachment member 24 may be movably attached to the second spinal prosthetic member 16 with the fastening device 20, as is now described.

In the non-limiting illustrated embodiment, the second spinal prosthetic member 16 includes a unitary body with laterally extending arms 40. Mounting hardware is positioned along the arms 40, such as but not limited to, a pair of screws 42 which can tighten hooks 44 against fusion rods 46, which may be attached to the second spinal structure 18 (e.g., pedicles in L4 and L5 in FIGS. 3 and 4) with pedicle screws 48. The second spinal prosthetic member 16 is formed with a non-straight interface 50, e.g., a concave surface, which articulates with extension 38 of the second attachment member 24.

In the non-limiting illustrated embodiment, the fastening device 20 includes a threaded fastener 52 and a spacer member 54. The spacer member 54 may have a non-straight surface that interfaces with and is tightened by the threaded fastener 52 against the non-straight surfaces of the first and second spinal prosthetic members 12 and 16.

The first and second spinal prosthetic members 12 and 16 may thus be pivotable with respect to one another about a first pivot axis 56 to define an angle A between the first and second spinal prosthetic members 12 and 16 that corresponds to a lordotic angle between the first and second spinal structures 14 and 18. The first and second spinal prosthetic members 12 and 16 may be pivoted in-situ. The fastening device 20, in its tightened position, fixes the first and second spinal prosthetic members 12 and 16 at a desired orientation along the non-straight surfaces thereof.

Optionally, the first and second spinal prosthetic members 12 and 16 may be further pivotable with respect to one another about a second pivot axis 60 angled at a non-zero angle with respect to the first pivot axis 56. This may provide further in-situ adjustment capability.

Although the invention has been described in conjunction with specific embodiments thereof, many alternatives, modifications and variations are apparent to those skilled in the art. Accordingly, all such alternatives, modifications and variations fall within the spirit and scope of the following claims.

What is claimed is:

1. Apparatus comprising:
  a first spinal prosthetic member attachable to a first spinal structure; and
  a second spinal prosthetic member attachable to a second spinal structure, said first and second spinal prosthetic members being movably attached to one another with a fastening device, said fastening device having a non-tightened position which permits rotational movement of said first and second spinal prosthetic members with respect to one another at a desired rotational orientation, and a tightened position which fixes said first and second spinal prosthetic members at the desired rotational orientation;
  wherein said first and second spinal prosthetic members are pivotable with respect to one another about a first pivot axis to define an angle between said first and second spinal prosthetic members that corresponds to a lordotic angle between the first and second spinal structures, and
  wherein said first and second spinal prosthetic members articulate with respect to one another along curved surfaces thereof and said fastening device, in its tightened position, fixes said first and second spinal prosthetic members at a desired rotational orientation along the curved surfaces, said fastening device comprising a threaded fastener and a spacer member, said spacer member having a curved surface that interfaces with and is tightened by said threaded fastener against the curved surfaces of said first and second spinal prosthetic members, and wherein said first spinal prosthetic member comprises a flexure assembly positioned between first and second attachment members, wherein flexure of said flexure assembly permits movement of the first attachment member relative to the second attachment member, said first attachment member comprising at least one attachment point attachable to the first spinal structure, and said second attachment member being movably attached to said second spinal prosthetic member with said fastening device, and wherein said second spinal prosthetic member comprises a unitary body that includes laterally extending arms comprising mounting hardware positioned along said arms.

2. The apparatus according to claim 1, wherein said first and second spinal prosthetic members are further pivotable with respect to one another around a second pivot axis angled at a non-zero angle with respect to the first pivot axis.

3. The apparatus according to claim 1, wherein said first spinal prosthetic member comprises a unitary body.

* * * * *